US007381538B2

(12) United States Patent
Reardon et al.

(10) Patent No.: US 7,381,538 B2
(45) Date of Patent: Jun. 3, 2008

(54) OPTICAL BIOSENSOR WITH ENHANCED ACTIVITY RETENTION FOR DETECTION OF HALOGENATED ORGANIC COMPOUNDS (75) Inventors: Kenneth F. Reardon, Fort Collins, CO (US); Neema Das, Murgeshpalya (IN)

(73) Assignee: Colorado State University Research Foundation (CSURF), Fort Collins, CO (US)

( * ) Notice: Subject to any disclaimer, the term of this patent is extended or adjusted under 35 U.S.C. 154(b) by 411 days.

(21) Appl. No.: 10/478,822

(22) PCT Filed: Jun. 1, 2002

(86) PCT No.: PCT/US02/17407

§ 371 (c)(1),
(2), (4) Date: Aug. 9, 2004

(87) PCT Pub. No.: WO03/025627

PCT Pub. Date: Mar. 27, 2003

(65) Prior Publication Data
US 2004/0265811 A1 Dec. 30, 2004

Related U.S. Application Data (60) Provisional application No. 60/295,211, filed on Jun. 1, 2001.

(51) Int. Cl.
C12Q 1/37 (2006.01)
(52) U.S. Cl. ...................................................... 435/23
(58) Field of Classification Search ...................... None
See application file for complete search history.

(56) References Cited

U.S. PATENT DOCUMENTS

| 4,739,380 A | 4/1988 | Lauks et al. .................. 357/25 |
| 5,152,758 A | 10/1992 | Kaetsu et al. ............. 604/890.1 |
| 5,156,810 A | 10/1992 | Ribi ........................ 422/82.01 |
| 5,177,012 A | 1/1993 | Kim et al. .................. 435/175 |
| 5,250,439 A | 10/1993 | Musho et al. .................. 435/25 |
| 5,541,057 A | 7/1996 | Bogart et al. .................. 435/5 |
| 5,629,214 A | 5/1997 | Crosby ....................... 436/518 |
| 5,698,083 A | 12/1997 | Glass ......................... 204/403 |
| 5,798,030 A * | 8/1998 | Raguse et al. ......... 204/403.08 |
| 5,837,196 A | 11/1998 | Pinkel et al. .................. 422/55 |
| 5,837,454 A | 11/1998 | Cozzette et al. ............... 435/6 |
| 5,972,199 A | 10/1999 | Heller et al. ............. 205/777.5 |
| 5,972,638 A | 10/1999 | Burlage et al. ............... 435/29 |
| 6,022,748 A | 2/2000 | Charych et al. ............ 436/527 |
| 6,060,327 A * | 5/2000 | Keen ...................... 204/403.14 |
| 6,159,681 A | 12/2000 | Zebala ........................ 435/4 |

OTHER PUBLICATIONS

Derek W. Campbell, entitled "The Development of Biosensors for the Detection of Halogenated Groundwater Contaminants," available from Morgan Library at the CSU in Fort Collins, Colorado, having been submitted by Derek W. Campbell in fulfillment of the requirements for the Degree of Master of Science at Colorado State University, Spring 1998 {labeled "Attachment B" of applicants' provisional app. filed Jun. 1, 2001 as containing general background technical information}.

Kenneth F. Reardon and Derek W. Campbell, "Biosensor for Halogenated Hydrocarbons," U.S. Appl. No. 60/099,890, filed Sep. 12, 1998 by Reardon and Campbell, 7 pages {labeled "Attachment C" of applicants' provisional app. filed Jun. 1, 2001 as containing general background technical information}.

Cord Müller. F. Schubert. T. Scheper, "Multicomponent fiberoptical biosensor for use in hemodialysis monitoring," Proc. SPIE vol. 2131, 555-562 Biomedical Fiber Optic Instrumentation(Jul. 1994) {referenced as "Cord Müller, et al." in applicants' provisional app. filed Jun. 1, 2001 for its general background technical information}.

J. Peter, W. Buchinger, F. Karner, and W. Hampel, "Characteristics of a microbial assay for the detection of halogenated hydrocarbons using cells of an actinomycete-like organism as a biological component," Acta Biotechnol 17 (1997) 2 pp. 123-130 Akademie Verlag.

Int'l Pub. No. WO 93/25892 (International app No. PCT/GB93/01216) ARS Holding / J. Attridge et al. "Sensor for Optical Assay".

* cited by examiner

Primary Examiner—Karen Cochrane Carlson
Assistant Examiner—Agnes B. Rooke
(74) Attorney, Agent, or Firm—Lathrop & Gage LC (57) ABSTRACT A distal tip, and associated method of producing, of a biosensor ion sensing transducer for use in detecting an analyte comprising an halogenated organic compound in an environment such as soil or an aqueous environment. Features include: a biocomponent comprising at least one enzyme for carrying out a dehalogenation of the compound; the biocomponent is immobilized to a surface of the tip; a treatment of the biocomponent for maintaining a period of enzymatic efficacy; and the biocomponent stabilized by means preferably selected from the group consisting of crosslinking a surface of the immobilized biocomponent, crosslinking a polymer layer to the biocomponent, adding a gel-hardening agent to the biocomponent, adding a stabilizing agent to the biocomponent, and modifying a component of the immobilizing means. Immobilization can be carried out by: (a) entrapment within a hydrogel; (b) entrapment within a polymeric network; (c) (micro)encapsulation; (d) covalent-bonding; and (e) adsorption. The dehalogenase of the biocomponent may be selected from the group consisting of hydrolases, subclass EC 3.8, and lyases, subclass EC 4.5 as listed in Table 2A.

18 Claims, 4 Drawing Sheets

OPTICAL BIOSENSOR WITH ENHANCED ACTIVITY RETENTION FOR DETECTION OF HALOGENATED ORGANIC COMPOUNDS

BACKGROUND OF THE INVENTION

This application claims priority under 35 USC §119(e) and 37 C.F.R. §1.78 to pending provisional patent application No. 60/259,211, filed 01 Jun. 2001.

In general, the present invention relates to techniques for monitoring halogenated organic chemicals (pollutants, pesticides, etc.) in soil, as well as groundwater, waste waters, and other aqueous environments. More particularly, the invention is directed to an improved distal tip having a transducer to which a biocomponent comprising a dehalogenase (selected for dehalogenation of a selected analyte of interest) is immobilized, treated, and/or stabilized for monitoring continuously in situ soil or an aqueous environment to detect the presence and/or concentration of the analyte, such as any of the s-triazine pesticides, including the chlorinated herbicide atrazine (used to control broadleaf and grassy weeds), simazine, terbuthylazine, propazine, cyanazine, deethylatrazine, and deisopropylatrazine, plus other s-triazines (including those in TABLE 1), lindane, and DDT. Disclosed is a novel technique of measuring an analyte and associated biosensor capable of measuring pH (hydrogen ion) and halide ion concentration in soil and aqueous environments to detect the concentration, or collect other information about, the analyte. In one aspect of the invention, focus is on a unique biosensor including a fiber optic element (an optical fiber or bundle), the tip of which has a layer of a bacteria atop a layer of a pH-sensitive fluorophore (dye). The bacteria is selected such that it carries an enzyme to catalyze a reaction with the halogenated compound of the analyte, releasing either protons (and causing a detectable pH change) or a measurable halide ion concentration. Further, prior to being 'glued' (immobilized or otherwise affixed) to the tip of the fiber optic transducer, the bacteria layer is specially treated and/or stabilized.

Currently available techniques to measure analytes, and more-particularly pollutants, in groundwater include ex situ laboratory measurements which generally have a long response time and are expensive, or use of immunoassay kits which can be quite inaccurate and also expensive. In Campbell, 1998 entitled "The Development of Biosensors for the Detection of Halogenated Groundwater Contaminants." Spring 1998, submitted by D. W. Campbell in fulfillment of the requirements for the Degree of Master of Science at Colorado State University, available from Morgan Library at the Colorado State University in Fort Collins, Colo., reference is made to a pH optode structure featuring the reaction illustrated schematically in Campbell, 1998 (labeled FIG. 2.4): the cleavage of halide ion $X^-$ and proton $H^+$ from a halogenated hydrocarbon by the appropriate hydrolytic dehalogenase. An earlier reference entitled "Multicomponent fiberoptical biosensor for use in hemodialysis monitoring" (Cord Muller, et al.) employed a pH optode-type biosensor structure limited to the use of urease as a catalyst (urea is split into ammonia & $CO_2$): the bifunctional reagent glutaraldehyde was used to bind the urease directly to the head of a pH optode.

Chemical biosensors are miniaturized analytical devices, which can deliver real-time and on-line information on the presence of specific compounds or ions in complex samples. Usually an analyte recognition process takes place followed by the conversion of chemical information into an electrical or optical signal. Two popular classes of chemical sensors used today are electrochemical transduction type. (amperometric, potentiometric, including ion-selective electrodes (ISE), field effect transistors (FETs), gas-sensing electrodes, etc., and conductimetric) and optical transduction type (including pH optodes). They are used during laboratory analysis as well as in industry, process control, physiological measurements, and environmental monitoring. The basic principles of operation of the chemical sensors utilizing electrochemical and optical transduction are quite well understood. In developing biosensors for general manufacture and commercial use, longevity and stabilization of the biocomponent are critical. It is preferable to have a stable, long-lived biosensor that can stand prolonged storage as well as perform well in use for a selected period of time. Among the biocomponent possibilities, enzymes, though very selective, fall on the lower end of the 'stability spectrum'.

The s-triazine compounds include many pesticides. Within the s-triazine family (which includes both pesticides and non-pesticide groups, see TABLE 1), atrazine is most widely used, although others include simazine, terbuthylazine, propazine, cyanazine, deethylatrazine, and deisopropylatrazine as well as others in FIG. 1, a depiction of several pathways derived from general knowledge of atrazine degradation. S-triazines are characterized by a symmetrical hexameric ring consisting of alternating carbon and nitrogen atoms.

TABLE 1

Non-pesticide s-triazine groups with comments about use and biodegradability.

Cyanuric acid

Cyanuric (isocyanuric) acids: N-Chlorination of Cyanuric acid at the R1, R2, and R3 sites yields chloroisocyanurates that are used as disinfectants (in swimming pools and hot-tubs), sanitizers (in household cleansers and automatic dishwashing compounds), and bleaches (in both the industrial and household bleaching of fabrics). The most common chloroisocyanurates are Trichloro and Dichloro isocyanuric acid(TCCA, DCCA) and Sodium dichloroisocyanuric acid (SDCC).

TABLE 1-continued

Non-pesticide s-triazine groups with comments about use and biodegradability.

SDCC: Triallyl isocyanurate (R1, R2, and R3 = propenyl) is used as a crosslinking agent for poly(vinyl chloride) and other systems.
Methylamine (also on the metapathway map) and N-substituted methylamines are sometimes used as finishing agents for textiles.

RDX: Nitramine explosives: Cyclotrimethylenetrinitramine (RDX) is an explosive and a propellant used in military rockets. The partial biodegradation of RDX by mixed microbial culture is reported in (Binks et al 1995).

Triazone: A cyclic urea used as a cross linking agent in textile finishing. 1,3-dimethylol-5-alkyltriazone is still widely used for this purpose. Cross linking agents are used in the preparation of textiles to induce "memory" and to add luster.

SUMMARY OF THE INVENTION

It is a primary object of the invention to provide structure and a method of producing a distal tip of a biosensor ion sensing transducer for use in detecting an analyte comprising an halogenated organic compound in an environment such as soil or an aqueous environment. The biocomponent being immobilized, treated, and stabilized accordingly.

As can be appreciated, the innovative biosensor, a distal tip of which has an ion sensing transducer for use in detecting an analyte and a biocomponent comprising a dehalogenase such as an enzyme selected from the hydrolases, class EC 3.8, or lyases, class EC 4.5, for carrying out a dehalogenation of the analyte—as contemplated and described herein—can accommodate a variety of enzymatic activities and distal tip structures, including features claimed herein, all within the spirit and scope of this disclosure. Advantages include, without limitation:

(a) Disposable use with real-time results—The invention may be used for single- or multiple-use applications, or for continuous real-time monitoring over a selected time period, of an aqueous or soil environment.

(b) Simplicity and versatility—The invention may be used to collect information about physical properties of a wide range of analytes without requiring sophisticated equipment and complicated procedures. Simplicity of design can lead to reduced fabrication costs making kits economically feasible for handy off-site use—allowing information to be readily available.

(c) Structural design—The unique combination of immobilization and stabilizing features provide a robust distal tip design.

(d) Several biosensor tips having similar transducer types (optical or electrochemical) may be incorporated into a bundle providing a package of different types of information relating to the environment by sampling simultaneously or sequentially.

Briefly described, once again, the invention includes a distal tip of a biosensor ion sensing transducer for use in detecting an analyte comprising an halogenated organic compound in an environment such as soil or an aqueous environment. The ion-sensing transducer is preferably selected from the following: a pH optode, a pH electrode, a field-effect transistor (FET), and an halide ion-selective electrode (ISE). Analytes of interest are many, including, without limitation: s-triazine compounds including those developed for use as pesticides such as atrazine, simazine, terbuthylazine, propazine, cyanazine, deethylatrazine, and deisopropylatrazine, and others including those listed in TABLE 1; beta-, or the more common, gamma-hexachlorocyclohexane ("Lindane"); and DDT (1,1,1-trichloro-2,2-bis(p-chlorophenyl)ethane). Microorganisms that can initiate pathways as identified in TABLE 3 are for the widely used herbicide atrazine (degradation example shown in FIG. 2), without limitation these include: *Pseudomonas* sp. ADP; *Ralstonia* sp. M91-3; *Clavibacter michiganese* sp. ATZ1; *Agrobacterium* sp. J14a; *Alcaligenes* sp. SG1; and *Rhodococcus* spp. NI86/21, TE1; *Pseudomonas* spp. 192, 194; and *Streptomyces* sp. PS1/5.

Key features of the distal tip include: a biocomponent comprising at least one enzyme for carrying out a dehalogenation of the compound; the biocomponent is immobilized to a surface of the tip; a treatment of the biocomponent for maintaining a period of enzymatic efficacy; and the biocomponent stabilized by means preferably selected from the group consisting of crosslinking a surface of the immobilized biocomponent, crosslinking a polymer layer to the biocomponent, adding a gel-hardening agent to the biocomponent, adding a stabilizing agent to the biocomponent, and modifying a component of the immobilizing means.

Immobilization is preferably carried out by means selected from the group consisting of (a) entrapment within a hydrogel; (b) entrapment within a polymeric network; (c) (micro)encapsulation; (d) covalent-bonding; and (e) adsorption. The dehalogenase may be selected from the group consisting of hydrolases, subclass EC 3.8, and lyases, subclass EC 4.5 as listed in TABLE 2A. One might choose to target a dehalogenase which (1) produces a measurable pH change and (2) needs no reactant other than the halogenated analyte (e.g., atrazine) and perhaps water—thus excluding the reductive dehalogenases, which require something to oxidize while they reduce the halogenated analyte, and other classes of enzymes that require oxygen or energy, from the cell.

Associated with the biosensor structural features, the invention also covers a method of producing a biosensor distal tip having an ion sensing transducer and a biocomponent for use in detecting an analyte (an halogenated organic compound) in an environment. In a first characterization of the method of the invention, steps include: immobilizing the biocomponent having at least one enzyme for carrying out a dehalogenation of the compound, to a surface of the tip by means selected from the group consisting of (a) entrapping the enzyme within a hydrogel secured to the tip surface; (b) entrapping the enzyme within a polymeric network secured to the tip surface; (c) (micro)encapsulating the enzyme; (d) covalent-bonding a second component of the biocomponent to the tip surface; (e) cross-linking the enzyme to a support material secured to the tip surface; and (f) adsorbing the enzyme into the tip surface; treating the biocomponent for maintaining a period of enzymatic efficacy; and stabilizing the biocomponent by means selected from the group consisting of crosslinking a polymer layer to the biocomponent, adding a gel-hardening agent to the biocomponent, adding a stabilizing agent to the biocomponent, and modifying a component of the immobilizing means.

Further distinguishing features of the biosensor distal tip and method of the invention are many. The hydrogel or polymeric matrix used for entrapment of the dehalogenase in the form of pure enzymes or within cells (whether naturally occurring or recombinant) may be selected as follows: suitable hydrogels include algal polysaccharides (such as agar, agarose, alginate, and K-carrageenan), gelatin, collagen, pectin, poly(carbamoyl) sulfonate, locust bean gum, and gellan; and suitable polymers include polyacrylamide, polystyrene, polymethacrylate, polyvinylalcohol and polyurethane. The biocomponent treatment may be selected from the following: applying an inhibitor of protein synthesis, adding a protease inhibitor, freeze drying, and dry heating. Further focusing on particular features: (1) the protein synthesis inhibitor may include any suitable antibiotic such as one selected from the following types: chloramphenicol, aminoglycosides (e.g., kanamycin), tetracyclines, and macrolides (e.g., erythromycin); (2) the polymer layer crosslinked for stabilization may be selected from suitable polymers including poly-L-lysine (PLL), polyethylenimine, polyacrylic acid, polyvinyl alcohol, polyacrylamide, and polyurethane; (3) a crosslinking agent such as glutaraldehyde may be used far the crosslinking of the biocomponent surface; (4) a suitable polyalcohol or sugar may be selected for adding to the biocomponent as a stabilizing agent.

BRIEF DESCRIPTION OF THE DRAWINGS

For purposes of illustrating the innovative nature plus the flexibility of design and versatility of the preferred structure and method of producing the biosensor distal tip disclosed hereby, the invention will be better appreciated by reviewing accompanying drawings (in which like numerals, if included, designate like parts). One can appreciate the many features that distinguish the instant invention from those known. The drawings have been included to communicate the features of the innovative structure and method of the invention by way of example, only, and are in no way intended to unduly limit the disclosure hereof.

DETAILED DESCRIPTION OF THE PREFERRED EMBODIMENTS

Biosensors have two key components: a biocomponent capable of sensing an analyte by producing some physical or chemical change in the analyte molecule; and a transducer, to which the biocomponent is immobilized, which converts this change into a measurable signal, whose magnitude is related to the concentration of the analyte of interest. The biocomponent preferably comprises a catalytic group such as an enzyme (whether utilized in purified form or in microorganisms and tissues). Enzymes are large, complex macromolecules, consisting largely of protein and usually containing a prosthetic group. As is well known, enzymes have catalytic activity, are highly specific to a particular substrate and are fairly fast acting. Typically the biosensor transducer is used to detect certain targeted by-products of the enzymatic reaction such as oxygen, ammonia, hydrochloric acid and carbon dioxide.

In spite of the many advantages of using an enzyme in a biocomponent, enzymes are quite sensitive to changes in pH, temperature, ionic strength, microorganisms and other biochemical factors in the microenvironments in which the biosensor is used. As a result, the enzyme(s) of a biocomponent can deactivate rapidly. Living cells contain at least a small amount of proteases which can, and do, degrade the intracellular proteins. Although pure enzymes are not exposed to potentially deactivating causes within a living cell of a microorganism, such as growth of unwanted proteases, there are tradeoffs: processes like extraction, isolation and purification of a particular enzyme from a complex cell environment can be expensive, tedious and complicated, as well as cause the enzyme to lose a high percentage of its activity.

Microorganisms are less expensive sources of enzymes than are purified enzymes and can aid in lowering the cost of biosensor production. The natural chemical composition of cells (whether recombinant or naturally produced) provides a useful environment for optimizing enzyme activity. However, living cells do require to a certain extent proper control of environment, maintenance and storage to retain their efficacy. Cell-based biosensors may have a longer response time and less specificity to a single analyte of interest due to the presence of other enzymes in the cells. Two known examples of cell-based sensors: a glucose sensor has been made using *Pseudomonas fluorescens* immobilized on an oxygen electrode; and another uses *Rhodococcus* sp. DSM 6344, is used to detect halogenated hydrocarbons. Like microorganisms, plant and animal tissues are enzyme-containing material that can be used to make cell-based biosensors. Antibodies are proteins that can bind with an antigen.

The nature of the interaction of the biological element with the analyte of interest impacts the choice of transduction technology. Transduction techniques can be categorized as follows:

Amperometric electrode (an electrochemical transducer)—A constant potential is maintained on the working electrode with respect to a reference electrode, and the current generated by the oxidation or reduction of an electroactive species at the surface of the working electrode is measured; the response is linear. The reference electrode need not be drift-free to have a stable response. Since the signal generated is highly dependent on the mass transfer of the electroactive species to the electrode surface, there can be a loss in sensitivity due to fouling by species that adsorb to the electrode surface. Enzymes, particularly oxidoreductases, are well suited to amperometric transduction as their catalytic activity is concerned with electron transfer. Electroactive species that can be monitored at the electrode surface include substrates of a biological reaction (e.g., $O_2$, NADH), final products (e.g., hydrogen peroxide for oxidase reactions, benzoquinone for phenol oxidation) and also electrochemical mediators that can directly transfer electrons from the enzyme to a working electrode surface (e.g. hexacyanoferrate, ferrocene, methylene blue).

Potentiometric electrode (an electrochemical transducer)—the potential difference between an active and a reference electrode is measured under the zero current flow condition. The three most commonly used potentiometric devices are ion-selective electrodes (ISEs), gas-sensing electrodes, and field-effect transistors (FETs). All these devices obey a logarithmic relationship between the potential difference and the activity of the ion of interest, thus, potentiometric electrode sensors have a wide dynamic range. One disadvantage of this transducer is the requirement of an extremely stable reference electrode. Ion-selective electrodes are commonly used to monitor aqueous environments (groundwater, waste water, etc.) FETs are commercially attractive as they can be used to build micro-biosensors according to currently available, widely used micro-electronic device production techniques.

Conductimetric electrode (an electrochemical transducer)—these electrodes are used to measure salinity of marine environments. In this technique, conductance is measured by the application of an alternating current between two noble-metal electrodes immersed in the solution. Due to specific enzyme reactions, they convert neutral substrates into charged products, causing a change in the conductance.

Optical Transducers Several types of photometric behavior are utilized by various opto-biosensors: ultraviolet-visible absorption, fluorescence (and phosphorescence) emission, bioluminescence, chemiluminescence, internal reflection spectroscopy (evanescent wave technology) and laser light scattering methods. When fluorescent reagents are utilized, a fluorescent substance is excited by incident light and as a result it emits light of longer wavelength. The intensity of emitted light changes when analyte binds with the fluorescent substance. The change in intensity can be measured as a response to a particular analyte. Suitable fluorescent reagents include trisodium 8-hydroxy-1, 3, 6-trisulphonate for pH sensors, fluoro (8-anilino-1-naphthalene sulphonate) for $Na^+$ ion sensor, and acridinium- and quinidinium-based reagents for halides. Chemiluminescence occurs by the oxidation of certain substances, usually with oxygen or hydrogen peroxide, to produce visible light. Bioluminescence is produced by certain biological substances, such as luciferins produced by firefly. Internal reflectance is a method based on the principle of total internal reflection of a light beam into an optically dense medium when the incident angle is greater than the critical angle. When such a process occurs, not all of the energy is confined in the optically dense medium. The internally reflected light generates an electromagnetic evanescent wave, which penetrates the lower density medium at the point of reflection, for a distance comparable to the wavelength of light. Techniques falling within the category of "light scattering": quasi-elastic light-scattering spectroscopy, photon correlation spectroscopy, and laser doppler velocimetry.

It is critical that the biocomponent be properly bound to the transducer; biocomponent immobilization techniques include:

Adsorption—The enzyme may be adsorbed onto one or more surface, partially or in whole, of the biocomponent material. Examples of materials to which enzymes may be adsorbed include: ion-exchange resins, ceramics, glass, polyvinyl chloride, chitin, chitosan, alumina, charcoal, glassy carbon, clay, cellulose, kaolin, silica gel, and collagen. Adsorption has been classified as physical adsorption (physisorption) and chemical adsorption (chemisorption). Physisorption is usually weak and occurs via the formation of van der Waals bonds or hydrogen bonds between the substrate and the enzyme molecules. Chemisorption is much stronger and involves the formation of covalent bonds.

(Micro)encapsulation—A thin microporous semipermeable membrane is used to surround the biocomponent. Because of the proximity between the biocomponent and the transducer and the very small membrane thickness, biosensor response can be maximized. Suitable materials for (micro)encapsulation include nylon and cellulose nitrate. Further bonding of the biocomponent to the transducer surface may be done using a conductive polymer (polypyrrole). The membrane may be selected for its ability to serve additional functions, such as selective ion permeability, enhanced electrochemical conductivity or mediation of electron transfer. Membrane types used for microencapsulation include: cellulose acetate, polycarbonate, collage, acrylate copolymers, poly(ethylene glycol) polytetrafluroethylene (PTFE), agarose, as well as alginate-polylysine-alginate microcapsule formed of alginate and polylysine.

Entrapment—Cells or the pure enzymes are physically constrained (entrapped) to stay inside a three-dimensional matrix. Suitable materials (both natural and synthetic) for entrapment include those that permit uniform cell distribution and have biocompatibility and good transport mechanisms, such materials include without limitation, alginate, agarose and collagen. One might also choose to utilize mild polymerization techniques for more-rugged immobilization. Hydrogels are preferably used as an agent for biosensor entrapment; they provide a hydrophilic environment for the biocomponent and they require only mild conditions to polymerize. Hydrogels can absorb large quantities of water, which can facilitate desirable reactions such as hydrolysis. Both natural and synthetic hydrogels are suitable for use. The naturally occurring algal polysaccharides (such as agar, agarose, alginate, and carrageenan) and synthetic polymers such as polyacrylamide, polystyrene and polyurethane, are examples of such suitable hydrogels. Synthetic polymers generally have a smaller pore size which can lead to less leakage of biocomponent, and hence longer stability; however, synthetics are generally toxic and the immobilization process is accompanied by generation of heat and production of free radicals. Natural polymers are generally non-toxic and biodegradable, and the immobilization process is less stressful to the biocomponent. On the down side, natural polymers may provide less mechanical strength and stability, and their larger pore size allows predation by protozoans and other soil or water dwelling predators, as well as degradation by hydrolase enzymes in the environment being tested.

Alginate, a hydrogel, provides a good, biocompatible microenvironment for the biocomponent with gentle encapsulation process. It is a naturally occurring linear polymer composed of $\beta$-(1,4) linked D-mannuronic acid and $\alpha$-(1, 4)-L-guluronic acid monomers. Commercially, alginate is obtained from kelp, but bacteria such as *Azotobacter vinelandii*, several *Pseudomonas* species and various algae also produce it. When alginate is exposed to $Ca^{+2}$ ions, a cross-linking network is formed by the bonding of $Ca^{+2}$ ions and polyguluronic portions of the polymer strand by a process known as ionic gelation. The gelation process is temperature-independent. Complete gelling time without cells may be as little as 30 minutes. Sol-gel technology has enabled extension of the entrapment principle to silicate networks that have some advantageous characteristics, such as require milder polymerization processes and matrices that exhibit good mass-transport and molecular-access properties, particularly for electrochemical and optical transduction modes.

Cross-linking—Here, the biocomponent is chemically bonded to solid supports or to another supporting material such as a gel. Bifunctional agents such as glutaraldehyde, hexamethylene diisocyanate and 1, 5-dinitro-2, 4-difluorobenzene may be used to bind the biocomponent to the solid support. While there is less leaching of the biocomponent and the layer tends to exhibit a long-term stability under more strenuous experimental conditions, such as exposure to flowing samples, stirring, washing, etc., cross-linking causes damage to the enzyme and may limit diffusion of the analyte in operation. By way of example, a tyrosinase biosensor for polyphenols was made by pretreating the electrode by polymerizing pyrrole in 0.1 M tetraethylammonium sulfonate on the surface. The tyrosinase solution and glutaraldehyde were then repetitively and alternately coated on the surface to cross-link the enzyme to the polypyrrole surface.

Covalent Bonding—Here, a particular group present in the biocomponent, which is not involved in catalytic action, is attached to the support matrix (transducer or membrane) by covalent bond. The radicals that take part in this reaction are generally nucleophilic in nature (e.g., —$NH_2$, —COOH, —OH, —SH and imidazole groups). In order to retain enzyme activity, the reaction should be performed under mild conditions. In order to protect the active site, the reaction is often carried out in the presence of a substrate. Materials suitable for covalent bonding include: Cellulose and cellulose derivatives; Silica; Glass; Dextran; Starch; Agarose; Porous silica; Chitin; Chitosan.

Lifetime—The active lifetime of a biosensor—its period of enzymatic efficacy—depends upon the type of biocomponent used. Sensor lifetime can vary from a few days to a few months. Generally, pure enzymes have the lowest stability while cell and tissue preparations have the longer lifetimes. There are three aspects of lifetime of a biosensor: (i) the active lifetime of the biosensor in use, (ii) the lifetime of biosensor in storage, and (iii) the lifetime of the biocomponent in storage prior to being immobilized.

Biosensors of the invention have a wide variety of applications: (A) Medical uses include disposable one-way sensors (assays) for routine blood, saliva and urine testing, and in vivo sensors for monitoring crucial parameters during surgery or in intensive care units. (B) Food and drink industry applications include contaminant detection, verification of product content (analyze glucose and sucrose concentrations), monitoring of raw material conversion and evaluation of product freshness. (C) Process control applications include monitoring pH, temperature and substrate and dissolved gas concentrations in various processes such as fermentation and microbial and cell growth. (D) Environmental monitoring applications include monitoring concentration and toxicity of contaminants (e.g., analytes such as heavy metals, pesticides, etc.) in surface and groundwater and in waste streams and in soils. (E) Defense and Security Industry applications include measuring the presence of chemical warfare agents such as nerve gases and mustard gas; detection of trace vapors, explosives and drugs.

TABLE 2A

Dehalogenating enzymes for use in biosensor of the invention.

| Enzyme name(s) | EC code | Known substrates (analytes) | Reference(s) |
| --- | --- | --- | --- |
| Enzyme subclass 3.8: hydrolases acting on halide bonds: | | | |
| alkyl-halide halidohydrolase(alkylhalidase, halogenase; haloalkane halidohydrolase; haloalkane dehalogenase) | 3.8.1.1 | Bromochloromethane | [1] |

TABLE 2A-continued

Dehalogenating enzymes for use in biosensor of the invention.

| Enzyme name(s) | EC code | Known substrates (analytes) | Reference(s) |
|---|---|---|---|
| 2-haloacid halidohydrolase (2-haloacid dehalogenase, 2-haloalkanoid acid halidohydrolase; 2-haloalkanoic acid dehalogenase; L-2-haloacid dehalogenase; DL-2-haloacid dehalogenase) | 3.8.1.2 | Acts on 2-haloacids of short chain lengths, C2 to C4 | [2] [3] |
| haloacetate halidohydrolase (haloacetate dehalogenase, monohaloacetate dehalogenase) | 3.8.1.3 | Fluoroacetate and other haloacetates | [4] [5] |
| L-thyroxine iodohydrolase (reducing) (thyroxine deiodinase, thyroxine 5-deiodinase; diiodothyronine 5'-deiodinase; iodothyronine outer ring monodeiodinase; iodothyronine 5'-deiodinase) | 3.8.1.4 | A group of enzymes, removing iodine atoms sequentially from thyroxine. | [6] [7] [8] |
| 1-haloalkane halidohydrolase (haloalkane dehalogenase, 1-chlorohexane halidohydrolase; 1-haloalkane dehalogenase) | 3.8.1.5 | Acts on a wide range of 1-haloalkanes, haloalcohols, haloalkenes and some haloaromatic compounds. | [9] [10] [11] |
| 4-chlorobenzoate chlorohydrolase (4-chlorobenzoate dehalogenase, halobenzoate dehalogenase) | 3.8.1.6 | 4-chlorobenzoate and other halogenated benzoates | [12] [13] |
| 4-chlorobenzoyl CoA chlorohydrolase (4-chlorobenzoyl-CoA dehalogenase) | 3.8.1.7 | Specific for dehalogenation at the 4-position. Can dehalogenate substrates bearing fluorine, chlorine, bromine and iodine in the 4-position. This enzyme is part of the bacterial 2,4-dichlorobenzoate degradation pathway. | [14] [15] |
| atrazine chlorohydrolase | 3.8.1.8 | Atrazine, simazine, and other halogenated s-triazines | [16] [17] |
| s-triazine hydrolase | 3.8.1.— | | |
| dichloroacetate halidohydrolase | 3.8.1.— | | |
| DL-2-haloacid dehalogenase | 3.8.1.— | | |
| 1,3,4,6-tetrachloro-1,4-cyclohexadiene halidohydrolase | 3.8.1.— | | |
| cis-chloroacrylic acid dehalogenase | 3.8.1.— | | |
| trans-chloroacrylic acid dehalogenase | 3.8.1.— | | |
| Enzyme subclass 4.5: lyases acting on carbon-halide bonds: | | | |
| DDT-dehydrochlorinase (DDT-ase) | 4.5.1.1 | DDT (1,1,1-trichloro-2,2-bis(4-chlorophenyl)ethane) | [18] [19] [20] |
| 3-chloro-D-alanine chloride-lyase (deaminating) (3-chloro-D-alanine dehydrochlorinase, B-chloro-D-alanine dehydrochlorinase) | 4.5.1.2 | 3-chloro-D-alanine | [21] [22] |
| dichloromethane chloride-lyase (chloride-hydrolysing) (dichloromethane dehalogenase) | 4.5.1.3 | Dichloromethane, dibromoethane, bromochloromethane, diiodomethane | [23] |
| L-2-amino-4-chloropent-4-enoate chloride-lyase (deaminating) (L-2-amino-4-chloropent-4-enoate dehydrochlorinase, L-2-amino-4-chloro-4-pentenoate dehalogenase) | 4.5.1.4 | L-2-amino-4-chloropent-4-enoate | [24] |
| 3-chloro-L-alanine chloride-lyase (adding thioglycolate) (S-carboxymethylcysteine synthase, S-carboxymethyl-L-cysteine synthase) | 4.5.1.5 | 3-chloro-L-alanine | [25] |
| halohydrin hydrogen-halide-lyase | 4.5.1.— | | |
| halohydrin hydrogen-halide-lyase B | 4.5.1.— | | |
| DDD dehydrochlorinase | 4.5.1.— | | |
| DDMS dehydrochlorinase | 4.5.1.— | | |
| gamma-hexachlorocyclohexane dehydrochlorinase | 4.5.1.— | | |
| 5-chloro-1,2,4-trihydroxybenzene dechlorinase | 4.5.1.— | | |
| Tribromobisphenol lyase | 4.5.1.— | | |

TABLE 2B

References for TABLE 2A (ordered in sequence as listed above)

Enzyme subclass 3.8: hydrolases acting on halide bonds (References as [numbered]):

[1] Heppel, L. A. and Porterfield, V. T. Enzymatic dehalogenation of certain brominated and chlorinated compounds. J. Biol. Chem. 176 (1948) 763-769.
[2] Goldman, P., Milne, G. W. A. and Keister, D. B. Carbon-halogen bond cleavage. 3. Studies on bacterial halidohyrolases. J. Biol. Chem. 243 (1968) 428-434. [Medline UI: 68123008]
[3] Motosugi, M., Esaki, N. and Soda, K. Preparation and properties of 2-halo acid dehalogenase from Pseudomonas putida. Agric. Biol. Chem. 46 (1982) 837-838.
[4] Goldman, P. The enzymatic cleavage of the carbon-fluorine bond in fluoroacetate. J. Biol. Chem. 240 (1965) 3434-3438.
[5] Goldman, P. and Milne, G. W. A. Carbon-fluorine bond cleavage. II. Studies on the mechanism of the defluorination of fluoroacetate. J. Biol. Chem. 241 (1966) 5557-5559. [Medline UI: 67053221]
[6] Chopra, I. J. and Teco, G. N. C. Characteristics of inner ring (3 or 5) monodeiodination of 3,5-diiodothyronine in rat liver: evidence suggesting marked similarities of inner and outer ring deiodinases for iodothyronines. Endocrinology 110 (1982) 89-97. [Medline UI: 82095045]
[7] Goswani, A., Leonard, J. L. and Rosenberg, I. N. Inhibition by coumadin anticoagulants of enzymatic outer ring monodeiodination of iodothyronines. Biochem. Biophys. Res. Commun. 104 (1982) 1231-1238. [Medline UI: 82182305]
[8] Smallridge, R. C., Burman, K. D., Ward, K. E., Wartofsky, L., Dimond, R. C., Wright, F. D. and Lathan, K. R. 3',5'-Diiodothyronine to 3'-monoiodothyronine conversion in the fed and fasted rat: enzyme characteristics and evidence for two distinct 5'-deiodinases. Endocrinology 108 (1981) 2336-2345. [Medline UI: 81188610]
[9] Keuning, S., Janssen, D. B. and Witholt, B. Purification and characterization of hydrolytic haloalkane dehalogenase from Xanthobacter autotrophicus GJ10. J. Bacteriol. 163 (1985) 635-639. [Medline UI: 85261076]
[10] Scholtz, R., Leisinger, T., Suter, F. and Cook, A. M. Characterization of 1-chlorohexane halidohydrolase, a dehalogenase of wide substrate range from an Arthrobacter sp. J. Bacteriol. 169 (1987) 5016-5021. [Medline UI: 88032819]
[11] Yokota, T., Omori, T. and Kodama, T. Purification and properties of haloalkane dehalogenase from Corynebacterium sp. strain m15-3. J. Bacteriol. 169 (1987) 4049-4054. [Medline UI: 87307981]
[12] Muller, R., Thiele, J., Klages, U. and Lingens, F. Incorporation of [18O]water into 4-hydroxybenzoic acid in the reaction of 4-chlorobenzoate dehalogenase from Pseudomonas sp. CBS 3. Biochem. Biophys. Res. Commun. 124 (1984) 178-182. [Medline UI: 85046491]
[13] Heppel, L. A., Porterfield, V. T. Enzymatic dehalogenation of certain brominated and chlorinated compounds. J. Biol. Chem. 176 (1948) 763-
[14] Chang, K. H., Liang, P. H., Beck, W., Scholten, J. D., Dunaway-Mariano, D. Isolation and characterization of the three polypeptide components of 4-chlorobenzoate dehalogenase from Pseudomonas sp. strain CBS-3. Biochemistry 31 (1992) 5605-5610. [Medline UI: 92304935]
[15] Crooks, G. P., Copley, S. D. Purification and characterization of 4-chlorobenzoyl CoA dehalogenase from Arthrobacter sp. strain 4-CB1. Biochemistry, 33 (1994) 11645-11649. [Medline UI: 95001870]
[16] de Souza, M. L., Wackett, L. P., Boundy-Mills, K. L., Mandelbaum, R. T. and Sadowsky, M. J. Cloning, characterization, and expression of a gene region from Pseudomonas sp. strain ADP involved in the dechlorination of atrazine. Appl. Environ. Microbiol. 61 (1995) 3373-3378. [Medline UI: 96035669]
[17] de Souza, M. L., Sadowsky, M. J. and Wackett, L. P. Atrazine chlorohydrolase from Pseudomonas sp. strain ADP: gene sequence, enzyme purification, and protein characterization. J. Bacteriol. 178 (1996) 4894-4900. [Medline UI: 96326334]

Enzyme subclass 4.5: lyases acting on carbon-halide bonds (References as [numbered]):

[18] Lipke, H. and Kearns, C. W. DDT dechlorinase. I. Isolation, chemical properties, and spectrophotometric assay. J. Biol. Chem. 234 (1959) 2123-2128.
[19] Lipke, H. and Kearns, C. W. DDT dechlorinase. II. Substrate and cofactor specificity. J. Biol. Chem. 234 (1959) 2129-2132.
[20] Moorefield, H. H. Purification of DDT-dehydrochlorinase from resistant houseflies. Contr. Boyce Thompson Inst. 18 (1956) 303-310.
[21] Nagasawa, T., Ishii, T. and Yamada, H. Physiological comparison of D-cysteine desulfhydrase of Escherichia coli with 3-chloro-D-alanine dehydrochlorinase of Pseudomonas putida CR 1-1. Arch. Microbiol. 149 (1988) 413-416. [Medline UI: 88251237]
[22] Yamada, H., Nagasawa, T., Ohkishi, H., Kawakami, B. and Tani, Y. Synthesis of D-cysteine from 3-chloro-D-alanine and hydrogen sulfide by 3-chloro-D-alanine hydrogen chloride-lyase (deaminating) of Pseudomonas putida. Biochem. Biophys. Res. Commun. 100 (1981) 1104-1110. [Medline UI: 81281807]
[23] Kohler-Staub, D. and Leisinger, T. Dichloromethane dehalogenase of Hyphomicrobium sp. strain DM2. J. Bacteriol. 162 (1985) 676-681. [Medline UI: 85182487]
[24] Moriguchi, M., Hoshino, S. and Hatanaka, S.-I. Dehalogenation and deamination of 1-2-amino-4-chloro-4-pentenoic acid by Proteus mirabilis. Agric. Biol. Chem. 51 (1987) 3295.
[25] Kumagai, H., Suzuki, H., Shigematsu, H. and Tuchikura, T. S-Carboxymethylcysteine synthase from Escherichia coli. Agric. Biol. Chem. 53 (1989) 2481-2487.

Stabilization of an immobilized biocomponent is important, whether a biosensor is to be stored for a prolonged period of time before use, in order to maximize performance of the biosensor to sense a selected ion (halide or hydrogen) in an environment. As mentioned, although enzymes are very selective and preferred here, enzymes share the disadvantage of low stability. As is the case in immobilization. stabilization technique depends on the biocomponent and type of transducer employed; techniques for stabilizing the biocomponent include:

Molecular Modification—The stability of enzymes can be improved by changing certain amino acids in the protein sequence—such as by site-directed mutagenesis, grafting of polysaccharides (or short chains of sugar molecules) onto the protein molecules, and other methods involving chemical and carbohydrate modifications.

Cross-Linking, Covalent Bonding, Entrapment, Encapsulation—These techniques considered useful as immobilization methods, can be used as supplements to the immobilization technique selected to improve enzyme stability by, for example: reducing the protein's mobility and thereby reducing degradation of its three-dimensional structure; or preventing loss of biocomponent from its immobilized matrix such as, when used in connection with an entrapment immobilization, by the addition of a selected gel-hardening agent such as glutaraldehyde, polyethyleneimine, hexamethylenediamine and formaldehyde.

Freeze Drying (Lyophilization)—This can provide for long-term preservation of microorganisms and enzymes. It involves removal of water from frozen bacterial suspensions by sublimation under reduced pressure. This process is performed in the presence of cryoprotective agents, such as glycerol and DMSO, which reduce the damage caused during freezing. Dried cells can be kept for a long period at 4° C. if kept away from oxygen, moisture and light and can be rehydrated and restored to their previous state. Two types of useful freeze drying include centrifugal freeze-drying and pre-freezing. Microorganisms that are sensitive to freeze drying can be dried using the liquid-drying method.

Heat Shock—This process involves heating vacuum-dried cells at a high temperature (~300° C.) for a very short time (~2-3 minutes). With the proper temperature and heating time selected for cell type, cells can be killed but retain a viable enzyme system. These dead cells can be kept for a long time away from moisture without any requirement of nutrients.

Addition of Carbohydrates and Polymers—Freeze-dried enzymes are often stabilized by the addition of stabilizers, such as polyalcohols and sugars like trehalose, maltose, lactose, sucrose, glucose and galactose. This stabilization is due to the interaction of the polyhydroxyl compound with water in the system. This effectively reduces interaction between protein and water and thereby strengthens the hydrophobic interactions of the protein molecule to its surroundings.

Freezing—The metabolic activities of a microorganism may be reduced by storing them at very low temperatures (−150° C. to −190° C.), achieved using liquid nitrogen.

Atrazine is one of the most commonly applied s-triazine herbicides (structure below):

TABLE 3

Altrazine degradation pathway map identifies organisms that can initiate the pathways given.

| Atrazine | Atrazine | Atrazine |
|---|---|---|
| *Pseudomonas* sp. ADP | *Rhodococcus* spp. NI86/21, TE1 | *Rhodococcus* spp. NI86/21, TE1 |
| *Ralstonia* sp. M91-3 | | |
| *Clavibacter* sp. | *Pseudomonas* spp. 192, 194 | *Pseudomonas* spp. 192, 194 |
| *Agrobacterium* sp.J14a | | |
| *Alcaligenes* sp. SG1 | *Streptomyces* sp. PS1/5 | *Streptomyces* sp. PS1/5 |
| atrazine chlorohydrolase ↓ | atrazine monooxygenase ↓ | atrazine monooxygenase ↓ |
| Hydroxyatrazine | Deisopropylatrazine | Deethylatrazine |
| | *Rhodococcus corallinus* NRRLB-15444R / *Nocardia* sp. | *Pseudomonas* spp. 192, 194 |
| hydroxy-atrazine ethylaminohydrolase | a-triazine hydrolase | deisopropyl-atrazine monooxygenase | deethyl-atrazine monooxygenase |

Figure 2:
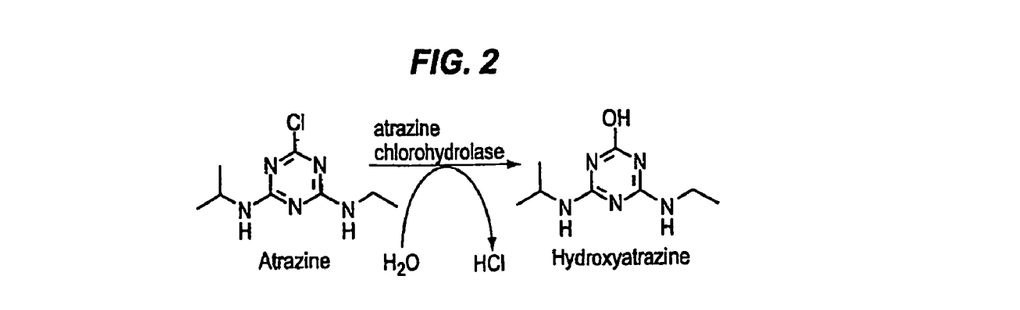
FIG. 2 depicts a hydrolytic dehalogenation of atrazine using atrazine chlorohydrolase.

FIG. 2 illustrates (see, also, left-hand column in above map) a hydrolytic dehalogenation of atrazine the first step of which can be carried out by several microorganism species, such as *Pseudomonas* sp. ADP, *Ralstonia* sp. M91-3, *Clavibacter* sp. ATZ1, *Agrobacterium* sp. J14a and *Alcaligenes* sp. SG1. The reaction depicted in the middle column in the above map represents an oxygenase attack on the isopropyl amino group; this reaction can be carried out by several microorganism species, such as *Rhodococcus* spp. NI86121 and TE1, *Pseudomonas* spp. 192 and 194 and *Streptomyces* sp. PS1/5. The reaction depicted in the right-hand column in the above map represents an oxygenase attack on the ethyl amino group; this reaction can be carried out by several species, such as *Rhodococcus* spp. N186121 and TE1; *Pseudomonas* spp. 192 and 194 and *Streptomyces* sp. PS 1/5.

EXAMPLE 1

Figure 3:
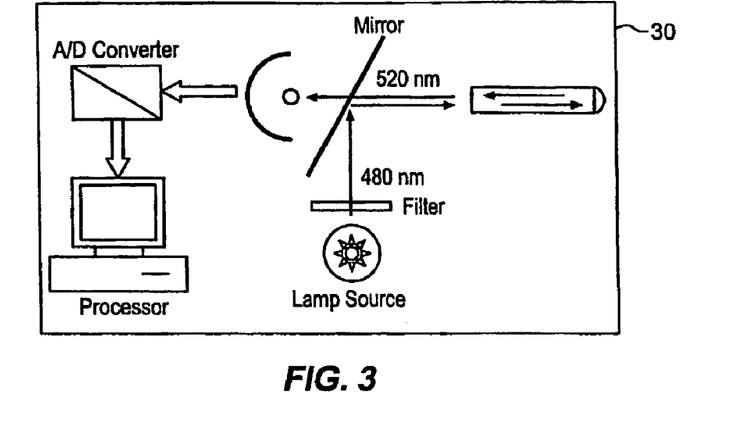
FIG. 3 schematically depicts features of a known system suitable for use in connection with employing a pH optode as the transducer [Campbell, 1998]. This fiber optic pH sensor system includes the pH optode with biocomponent, a lens focusing system, a photomultiplier (PMT), an A/D convener and suitable microprocessor.
Figure 4:
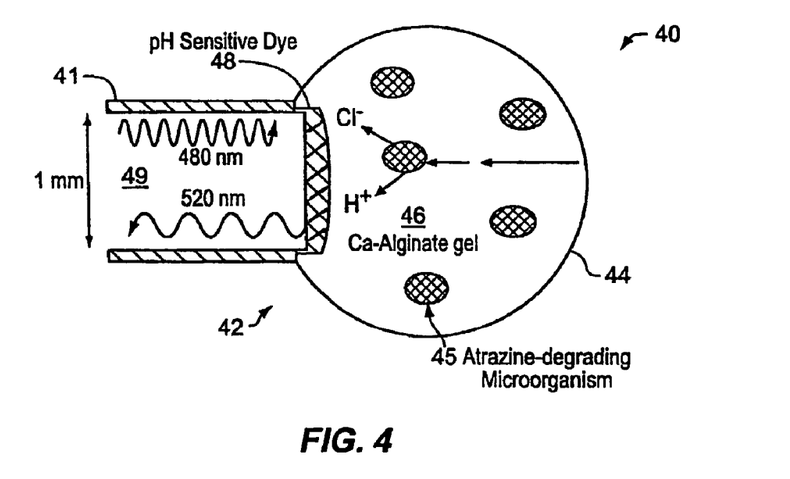
FIG. 4 schematically depicts features of the improved distal tip of the invention, an embodiment utilizing a pH optode to which the dehalogenase has been immobilized by means of entrapment within a hydrogel or polymer matrix, as shown bulbous/enlarged for clarity.

Biosensor employing pH optode with biocomponent, dehalogenase carried by whole cells immobilized by gel entrapment (for reference, see FIGS. 3 and 4). Distal tip section was coupled to a 1-m long polymethylmethacrylate (PMMA) fiber optic cable. Cells stored at 4° C. in phosphate-buffered saline were centrifuged at 15,000×g for 2 min.; the pellet was then washed twice with saline (9 g/L of NaCl [pH 7.1]) containing 50 µg/mL of chloramphenicol. Next, sodium-alginate (4% w/v in water) containing about 100 µg/mL of chloramphenicol was added and mixed well with the cell pellet. This cell—alginate mixture was kept for 5 minutes at room temperature before it was used to make the biosensor. The cell-alginate mixture was stirred well with a pipette tip and a small drop of gel was carefully deposited on the tip of the pH optode. The tip was dipped into an ice-cold solution of 7% (w/v) of $CaCl_2.2H_2O$ for 15 minutes. When exposed to $Ca^{+2}$ ions, a cross-linking network was formed by the bonding of $Ca^{+2}$ ions and polyguluronic portions of the polymer strand by a process known as ionic gelation. After immobilization, the tip was about 2 mm in diameter. A protease inhibitor cocktail in 1 mL of saline solution was prepared by adding 215 mg of lyophilized protease inhibitor in a solution containing 1 mL of DMSO (Dimethyl sulfoxide) and 4 mL of deionized water. The cocktail had a broad specificity for the inhibition of serine, cysteine, aspartic and metalloproteases, and aminopeptidases.

EXAMPLE 2

The alginate bead was coated with poly-L-lysine (PLL). First, a biosensor was prepared with microorganism strain ADP. The Ca—alginate bead on the biosensor tip (nearly 1 mm) was washed twice with saline solution (9 g/L of NaCl in water). The biosensor tip was immersed in 10 mL of 0.4% (w/v) of poly-L-lysine. HCl solution in saline for 30 min. at 30° C. In order to remove unreacted PLL from the bead surface, tip was washed with saline solution.

EXAMPLE 3

Two microorganisms suitable for use in degrading atrazine are *Pseudomonas* sp. strain ADP and *Clavibacter michiganese* ATZ1. Studies have shown that strain ADP has three genes (atz-A, atz-B and atz-C) that encode enzymes responsible for the degradation of atrazine to cyanuric acid. Strain ATZ1 has 100% homology only with atz-A; and thus only carries out reactions similar to the first two steps of strain ADP. For further reference, see tables below:

TABLE 8.1

Physical methods used to design a biosensor

| | |
|---|---|
| PHYSICAL TRANSDUCER | Optical transduction: fluorescent dye |
| IMMOBILIZATION METHOD | Entrapment: Ca-alginate gel matrix, time of gelation = 20 minutes |
| BIOCOMPONENT | Whole cell of atrazine degrading strain: treated under various conditions |
| STABILIZATION METHOD | Storage in refrigerator at 4° C. |
| SIZE | Less than 2 mm diameter of immobilized gel: cell density ~1 g of wet wt. of cells/wt. of alginate |

TABLE 8.2

Summary of sensitivity parameters for the biosensor

| Microorganism used as a biocomponent | Linear Range (ppb) | Detection Limit | Response Time (90% of response for change of 25 ppb of atrazine conc., ~2 mm bead dia.) | Reproducibility (standard deviation based on 3 measurements) |
|---|---|---|---|---|
| ADP | 0-125 | <1 ppb | 19.7 ± 2.5 | <6% |
| ATZ1 | 0-100 | <1 ppb | 10.7 ± 2.3 | <5% |

TABLE 8.4

Summary of results of activity retention of the biosensor using different types of biocomponents.

| Type of microorganism Used as biocomponent | Activity retention >90% (days) | Activity retention >30% (days) |
|---|---|---|
| ADP | 5 | 7 |
| Heat-treated ADP | 7 (dry heating time = 30 sec) | 11 |
| | 9 (dry heating time = 60 sec) | 12 |
| Chloramphenicol- treated ADP | 8 (Conc. of chloramphenicol = 50 μg/mL) | 9-10 |
| | 10 (Conc. of chloramphenicol = 200 μg/mL) | 60% activity retention on the 12th day. |
| Protease inhibitor- treated ADP | 6 | 10 |
| ATZ1 | 5 | 11 |

Figure 1:
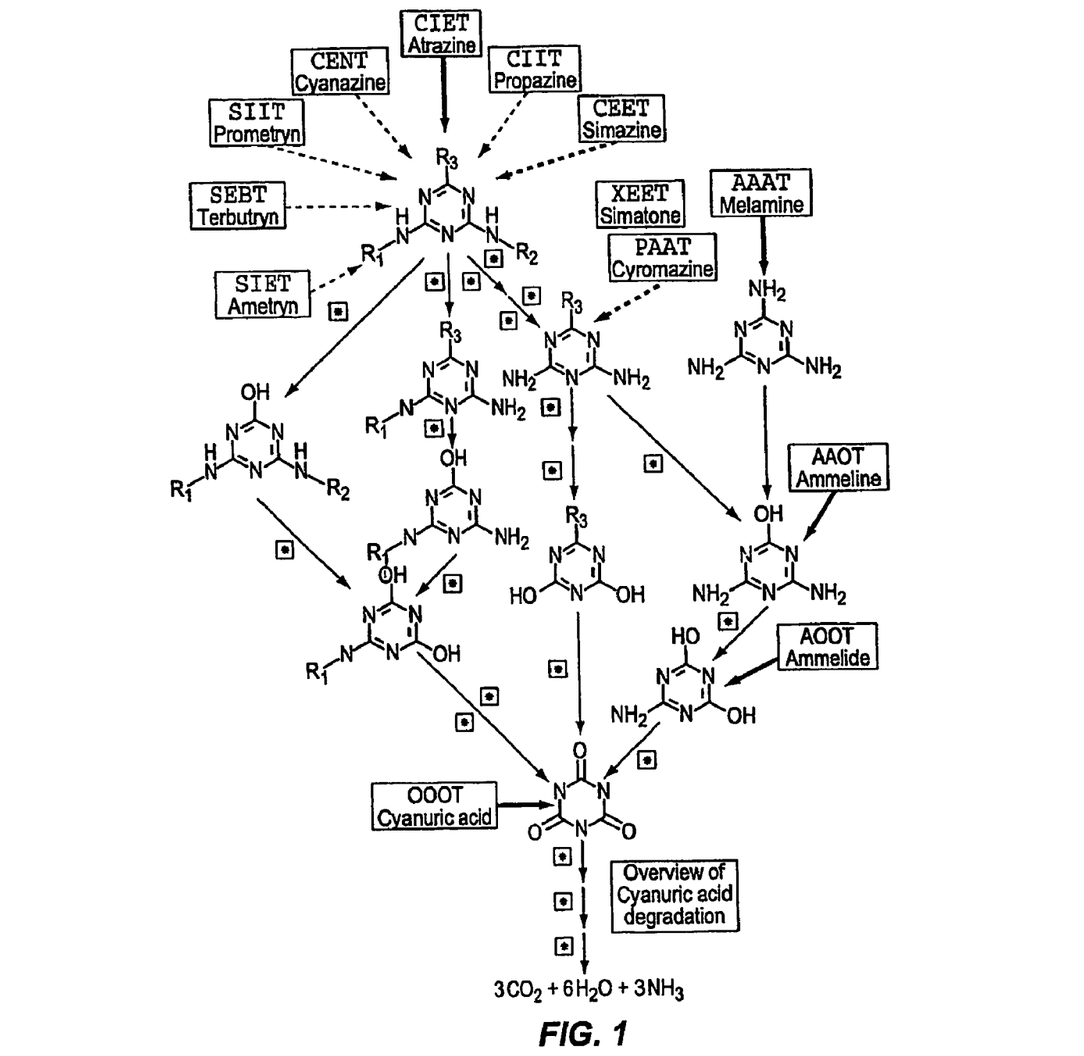
FIG. 1 is a depiction of several pathways derived from general knowledge of the degradation of the s-triazine, atrazine.

Once again, turning to the figures: FIG. 1 is a depiction of several pathways derived from general knowledge of the degradation of the s-triazine, atrazine. FIG. 2 depicts a hydrolytic dehalogenation of atrazine using atrazine chlorohydrolase. FIG. 3 schematically depicts features of a known system 30 suitable for use in connection with employing a pH optode as the transducer [Campbell, 1998]. This fiber optic pH sensor system 30 includes the pH optode with biocomponent, a lens focusing system, a photomultiplier (PMT), an A/D converter and suitable microprocessor. FIG. 4 schematically depicts features of the improved distal tip 42 of the invention, an embodiment utilizing a pH optode 49 to which biocomponent 44 comprising the dehalogenase 45 (either in pure form or carried in a microorganism at 45) has been immobilized by means of entrapment within a hydrogel or polymer matrix (at 46), as shown bulbous/ enlarged for clarity. The pH optode 49 has suitable cladding 41 for purposes of protecting the fiber(s) of the optical element (single or bundle) therewithin. Information about the environment 40 (soil or aqueous, for example) can be collected according to the invention, all as disclosed hereby.

Figure 5:
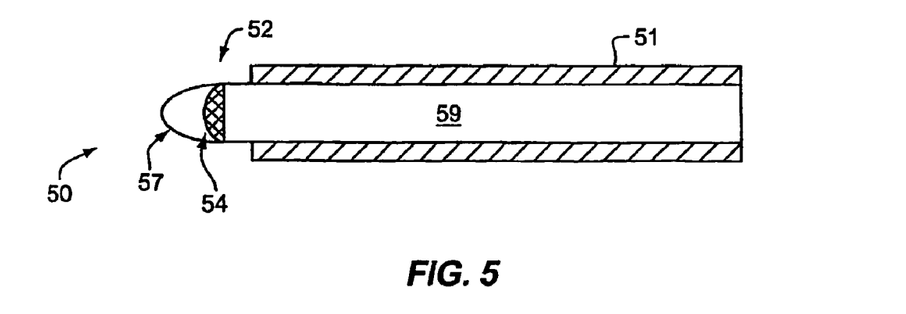
FIG. 5 schematically depicts features of a distal tip embodiment of the invention wherein two different matrices of a hydrogel or polymer are superimposed—the layer adjacent the distal tip surface preferably having a higher concentration of dehalogenase (whether carried by whole cells or in pure form) than the outermost layer.

FIG. 5 schematically depicts features of a distal tip 52 embodiment of the invention wherein two different matrices of a hydrogel or polymer are superimposed—the layer adjacent the distal tip 54 surface preferably having a higher concentration of dehalogenase (whether carried by whole cells or in pure form) than the outermost layer 57. The pH optode 59 has suitable cladding 51 for purposes of protecting the fiber(s) of the optical element (single or bundle) therewithin. Information about the environment 50 (soil or aqueous, for example) can be collected according to the invention, all as disclosed hereby.

Figure 6:
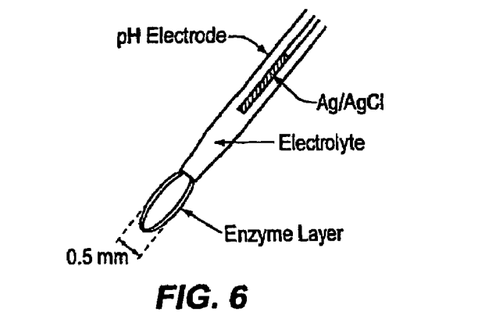
FIG. 6 schematically depicts features of a distal tip embodiment of the invention employing a pH microelectrode transducer, an enzyme-containing biocomponent immobilized to the distal tip.
Figure 7:
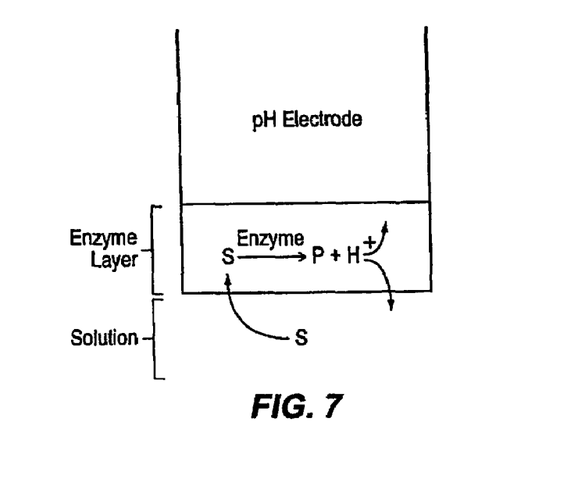
FIG. 7 schematically represents further details of the pH electrode depicted in FIG. 6, featuring the reaction within the enzymatic layer of the analyte of interest (here, S, for 'substrate') in general terms—the diffusion of S resulting in products P and $H^+$—as is well known.
Figure 8:
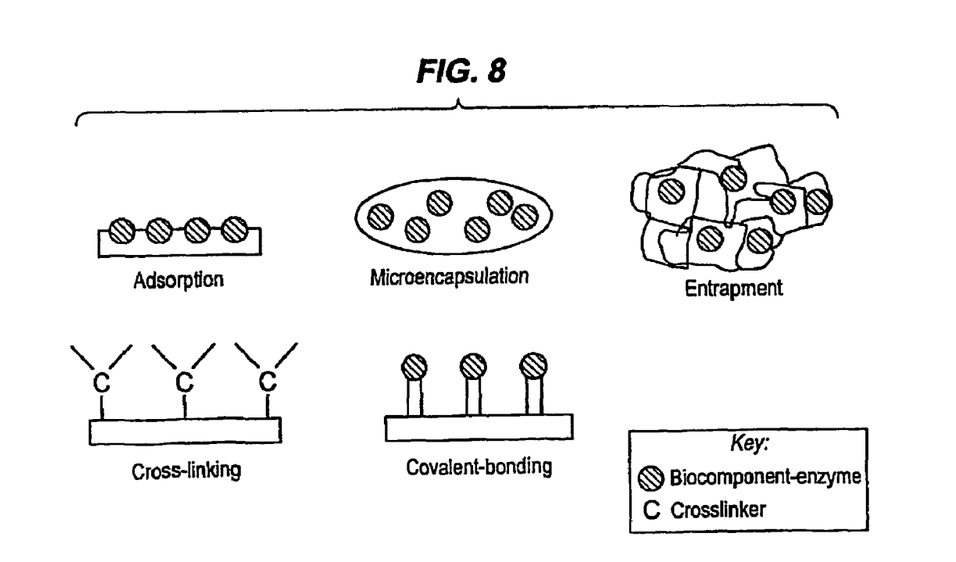
FIG. 8 schematically represents several immobilization techniques as identified according to the invention.
Figure 9:
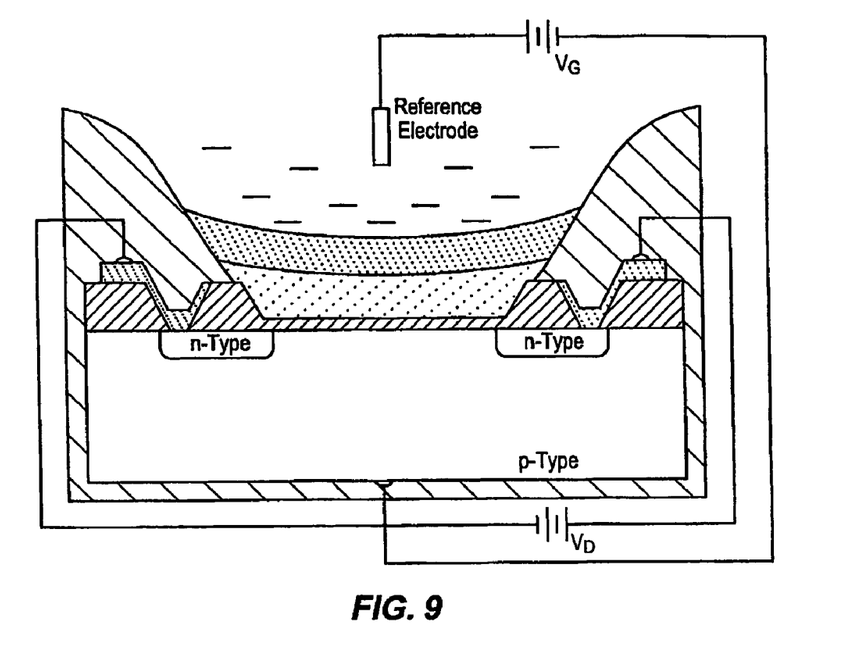
FIG. 9 schematically depicts features of a micro-sized embodiment of the invention wherein the transducer employed is a Field Effect Transistor (FET) type to which a biocomponent is immobilized.
Figure 10:
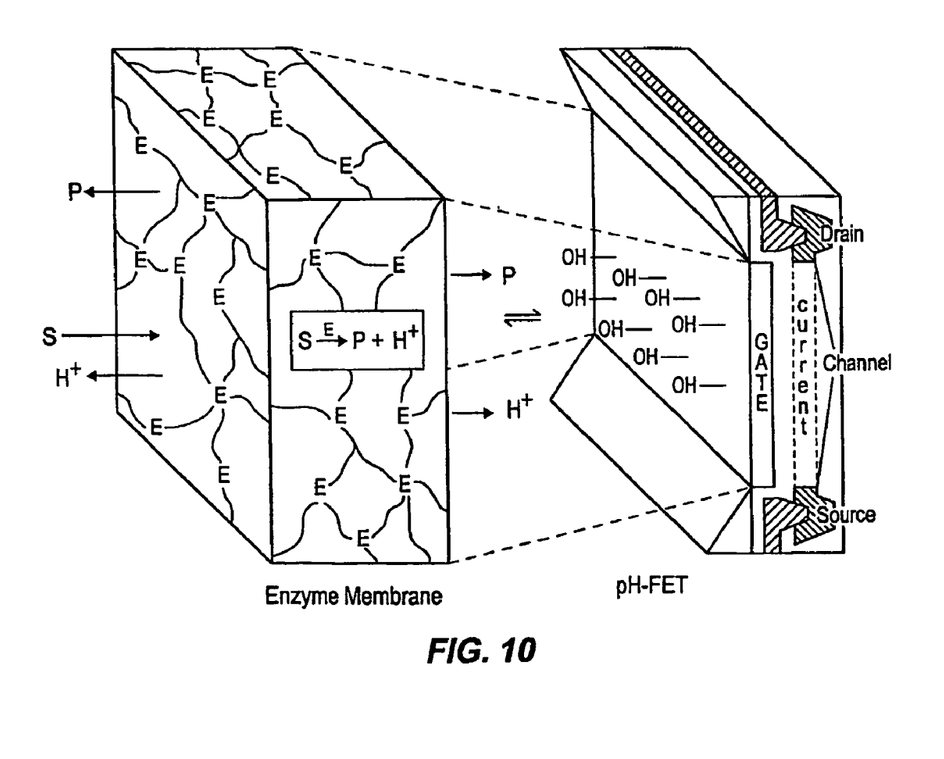
FIG. 10 schematically represents further details of the pH-sensitive FET transducer depicted in FIG. 9, featuring the reaction within the enzymatic layer of the analyte of interest (here, S, for 'substrate') in general terms-the diffusion of S resulting in products P and $H^+$—as is well known.

FIG. 6 schematically depicts features of a distal tip embodiment of the invention employing a pH microelectrode transducer, an enzyme-containing biocomponent immobilized to the distal tip. FIG. 7 schematically represents further details of the pH electrode depicted in FIG. 6, featuring the reaction within the enzymatic layer of the analyte of interest (here, S, for 'substrate') in general terms—the diffusion of S resulting in products P and $H^+$—as is well known. FIG. 8 schematically represents several immobilization techniques as identified according to the invention. FIG. 9 schematically depicts features of a micro-sized embodiment of the invention wherein the transducer employed is a Field Effect Transistor (FET) type to which a biocomponent is immobilized. FIG. 10 schematically represents further details of the pH-sensitive FET transducer depicted in FIG. 9, featuring the reaction within the enzymatic layer of the analyte of interest (here, S, for 'substrate') in general terms—the diffusion of S resulting in products P and $H^+$—as is well known.

As one can appreciate, feature details for a method to produce a distal tip of the invention are readily ascertainable by reviewing the accompanying figures and supporting text such that further visual depiction is unnecessary.

While certain representative embodiments and details have been shown merely for the purpose of illustrating the invention, those skilled in the art will readily appreciate that various modifications may be made to these representative embodiments without departing from the novel teachings or scope of this invention. Accordingly, all such modifications are intended to be included within the scope of this invention as defined in any illustrative-claim included below. Although the commonly employed preamble phrase "comprising the steps of" may be used herein, or hereafter, in a method claim, the Applicants in no way intend to invoke 35 U.S.C. Section 112 §6. Furthermore, in any claim that is filed hereafter (as well as any claim included herewith for illustrative purposes), any means-plus-function clauses used, or later found to be present, are intended to cover the structures described herein as performing the recited function and not only structural equivalents but also equivalent structures.

What is claimed is:

1. A distal tip of a biosensor ion sensing transducer for use in detecting an analyte comprising a halogenated organic compound, the tip comprising:

a biocomponent comprising at least one enzyme selected from the group consisting of hydrolases, subclass EC 3.8, and lyases, subclass EC 4.5, for carrying out a dehalogenation of the compound, said biocomponent immobilized to a surface of the tip by means selected from the group consisting of (a) entrapment within a hydrogel; (b) entrapment within a polymeric network; (c) encapsulation; (d) covalent-bonding; and (e) adsorption;

wherein said biocomponent has been treated to maintain a period of enzymatic efficacy; and wherein said biocomponent is stabilized to said tip by means selected from the group consisting of crosslinking a surface of said immobilized biocomponent, crosslinking a polymer layer to said biocomponent, adding a gel-hardening agent to said biocomponent, adding a stabilizing agent to said biocomponent, and modifying a component used to immobilize said biocomponent to said surface of the tip.

2. The distal tip of claim 1, said immobilization means comprising entrapment within said hydrogel, wherein said hydrogel is selected from the group consisting of algal polysaccharides, gelatin, collagen, pectin, poly(carbamoyl) sulfonate, locust bean gum, and gellan.

3. The distal tip of claim 1, further comprising an ion-sensing transducer selected from the group consisting of a pH optode, a pH electrode, a field-effect transistor (FET), and a halide ion-selective electrode (ISE).

4. The distal tip of claim 1, said biocomponent stabilized to said tip by crosslinking the polymer layer, wherein said crosslinked polymer layer is selected from the group consisting of poly-L-lysine, polyethylenimine, polyacrylic acid, polyvinyl alcohol, polyacrylamide, and polyurethane.

5. The distal tip of claim 1 wherein said hydrolases, subclass EC 3.8, comprise the enzymes selected from the group consisting of:
   alkyl-halide halidohydrolase,
   2-haloacid halidohydrolase,
   haloacetate halidohydrolase,
   1-halo alkane halidohydrolase,
   4-chlorobenzoate chlorohydrolase,
   4-chlorobenzoyl CoA chlorohydrolase,
   atrazine chlorohydrolase,
   s-triazine hydrolase,
   dichloroacetate halidohydrolase,
   DL-2-haloacid dehalogenase,
   1,3,4,6-tetrachloro-1,4-cyclohexadiene halidohydrolase,
   cis-chloroacrylic acid dehalogenase, and
   trans-3-chloroacrylic acid dehalogenase;
   and said lyases, subclass EC 4.5, comprise the enzymes selected from the group consisting of:
   DDT-dehydrochlorinase (DDT-ase),
   3-chloro-D-alanine chloride-lyase (deaminating),
   dichloromethane chloride-lyase (chloride-hydrolysing),
   L-2-amino-4-chloropent-4-enoate chloride-lyase (deaminating),
   3-chloro-L-alanine chloride-lyase (adding thioglycolate),
   halohydrin hydrogen-halide-lyase A,
   halohydrin hydrogen-halide-lyase B,
   DDD dehydrochlorinase,
   DDMS dehydrochlorinase,
   gamma-hexachlorocyclohexane dehydrochlorinase, and
   5-chloro-1,2,4-trihydroxybenzene dechlorinase.

6. The distal tip of claim 1, wherein said biocomponent is treated according to a treatment selected from the group consisting of applying an inhibitor of protein synthesis, adding a protease inhibitor, freeze drying, and dry heating.

7. The distal tip of claim 6, wherein the protein synthesis inhibitor is selected from the group of antibiotics consisting of chloramphenicol, aminoglycosides, tetracyclines, and macrolides.

8. The distal tip of claim 1, said biocomponent stabilized to said tip by crosslinking the surface of said immobilized biocomponent using a crosslinking agent, wherein the crosslinking agent comprises glutaraldehyde.

9. The distal tip of claim 1, wherein said biocomponent is selected from whole isolated cells, purified enzymes, and combinations thereof.

10. A distal tip of a biosensor ion sensing transducer for use in detecting an analyte comprising a halogenated organic compound, the tip comprising:
    a biocomponent comprising at least one enzyme selected from the group consisting of hydrolases, subclass EC 3.8, and lyases, subclass EC 4.5, for carrying out a dehalogenation of the compound, said biocomponent immobilized to a surface of the tip by means selected from the group consisting of (a) entrapment within a hydrogel; (b) entrapment within a polymeric network; (c) encapsulation; (d) covalent-bonding; and (e) adsorption,
    wherein said biocomponent is stabilized to said tip by means selected from the group consisting of crosslinking a surface of said immobilized biocomponent, crosslinking a polymer layer to said biocomponent, adding a gel-hardening agent to said biocomponent, adding a stabilizing agent to said biocomponent, and modifying a component used to immobilize said biocomponent to said surface of the tip.

11. The distal tip of claim 10, said immobilization means comprising entrapment within said hydrogel, wherein said hydrogel is selected from the group consisting of algal polysaccharides, gelatin, collagen, pectin, poly (carbamoyl) sulfonate, locust bean gum, and gellan.

12. The distal tip of claim 10, further comprising an ion-sensing transducer selected from the group consisting of a pH optode, a pH electrode, a field-effect transistor (FET), and a halide ion-selective electrode (ISE).

13. The distal tip of claim 10, said biocomponent stabilized to said tip by crosslinking the polymer layer, wherein said crosslinked polymer layer is selected from the group consisting of poly-L-lysine, polyethylenimine, polyacrylic acid, polyvinyl alcohol, polyacrylamide, and polyurethane.

14. The distal tip of claim 10 wherein said hydrolases, subclass EC 3.8, comprise the enzymes selected from the group consisting of:
    alkyl-halide halidohydrolase,
    2-haloacid halidohydrolase,
    haloacetate halidohydrolase,
    1-haloalkane halidohydrolase,
    4-chlorobenzoate chlorohydrolase,
    4-chlorobenzoyl CoA chlorohydrolase,
    atrazine chlorohydrolase,
    5-triazine hydrolase,
    dichloroacetate halidohydrolase,
    DL-2-haloacid dehalogenase,
    1,3,4,6-tetrachloro-1,4-cyclohexadiene halidohydrolase,
    cis-chloroacrylic acid dehalogenase, and
    trans-3-chloroacrylic acid dehalogenase;
    and said lyases, subclass EC 4.5, comprise the enzymes selected from the group consisting of:
    DDT-dehydrochlorinase (DDT-ase),
    3-chloro-D-alanine chloride-lyase (deaminating),
    dichloromethane chloride-lyase (chloride-hydrolysing),
    L-2-amino-4-chloropent-4-enoate chloride-lyase (deaminating),
    3-chloro-L-alanine chloride-lyase (adding thioglycolate),
    halohydrin hydrogen-halide-lyase A,
    halohydrin hydrogen-halide-lyase B,
    DDD dehydrochlorinase,
    DDMS dehydrochlorinase,
    gamma-hexachlorocyclohexane dehydrochlorinase, and
    5-chloro-1,2,4-trihydroxybenzene dechlorinase.

15. The distal tip of claim 10, wherein said biocomponent is treated to maintain a period of enzymatic efficacy according to a treatment selected from the group consisting of applying an inhibitor of protein synthesis, adding a protease inhibitor, freeze drying, and dry heating.

16. The distal tip of claim 15, wherein the protein synthesis inhibitor is selected from the group of antibiotics consisting of chloramphenicol, aminoglycosides, tetracyclines, and macrolides.

17. The distal tip of claim 10, said biocomponent stabilized to said tip by crosslinking the surface of said immobilized biocomponent using a crosslinking agent, wherein the crosslinking agent comprises glutaraldehyde.

18. The distal tip of claim 10, wherein said biocomponent is selected from whole isolated cells, purified enzymes, and combinations thereof.

* * * * *